US007775205B2

(12) United States Patent
Edgerley

(10) Patent No.: US 7,775,205 B2
(45) Date of Patent: Aug. 17, 2010

(54) MEDICAMENT DISPENSER

(75) Inventor: David Anthony Edgerley, London (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1180 days.

(21) Appl. No.: 10/492,457

(22) PCT Filed: Oct. 9, 2002

(86) PCT No.: PCT/EP02/11311

§ 371 (c)(1),
(2), (4) Date: Apr. 14, 2004

(87) PCT Pub. No.: WO03/035151

PCT Pub. Date: May 1, 2003

(65) Prior Publication Data

US 2005/0228341 A1    Oct. 13, 2005

(30) Foreign Application Priority Data

Oct. 19, 2001    (GB)    ................................. 0125134.7

(51) Int. Cl.
*A61M 15/00*    (2006.01)
*A61M 16/00*    (2006.01)
(52) U.S. Cl. ............................. 128/203.21; 128/203.23; 128/203.15; 128/200.14; 128/205.21; 128/207.14; 221/69; 221/70; 221/71; 221/74; 221/83; 206/530; 206/531; 206/532
(58) Field of Classification Search ............ 128/200.23, 128/203.15, 203.18, 203.19, 203.21, 205.23; 221/71, 73, 69
See application file for complete search history.

(56) References Cited

U.S. PATENT DOCUMENTS

| 4,668,722 | A | * | 5/1987 | Mack .......................... 524/103 |
| 4,940,966 | A | | 7/1990 | Pettigrew et al. |
| 5,590,645 | A | | 1/1997 | Davies et al. |

(Continued)

FOREIGN PATENT DOCUMENTS

WO    WO 92/12402    7/1992

(Continued)

OTHER PUBLICATIONS

Dooner et al., 1995, The Kinematic Geometry of Gearing, A Concurrent Engineering Approach; Chapter 1, Introduction to the Kinematics of Gearing, 1.1-1.8, pp. 3-15.*

(Continued)

*Primary Examiner*—Justine R Yu
*Assistant Examiner*—Clinton Ostrup
(74) *Attorney, Agent, or Firm*—James P. Riek

(57) ABSTRACT

There is provided a medicament dispenser for use with a medicament carrier having a plurality of pockets for containing medicament wherein said pockets are spaced along the length of and defined between two peelable sheets secured to each other, said dispenser having an internal mechanism for accessing said medicament contained within said medicament carrier. The internal mechanism comprises a carrier drive means; indexing means and clutch means, in communication therebetween. The clutch means comprises a gearing surface defining plural gear engagement positions; and plural gear teeth for engaging said plural gear engagement positions. The plural gear teeth are arranged such that at any one time only a single gear tooth engages a single gear engagement position.

37 Claims, 10 Drawing Sheets

U.S. PATENT DOCUMENTS

| | | | |
|---|---|---|---|
| 5,619,984 A * | 4/1997 | Hodson et al. | 128/203.15 |
| 5,873,360 A * | 2/1999 | Davies et al. | 128/203.15 |
| 6,014,969 A | 1/2000 | Lloyd et al. | |
| 6,032,666 A | 3/2000 | Davies et al. | |
| 6,880,722 B2 * | 4/2005 | Anderson et al. | 221/71 |
| 2004/0094152 A1 * | 5/2004 | Harvey et al. | 128/203.15 |

FOREIGN PATENT DOCUMENTS

| | | |
|---|---|---|
| WO | WO 96/31790 | 10/1996 |
| WO | WO 9841255 A2 * | 9/1998 |
| WO | WO 01/41846 | 6/2001 |
| WO | WO 01/96181 A1 * | 12/2001 |
| WO | WO 02/36189 | 5/2002 |

OTHER PUBLICATIONS

Dooner et al., 1995, The Kinematic Geometry of Gearing, A Concurrent Engineering Approach; Chapter 1, Introduction to the Kinematics of Gearing, chapter 9, p. 374.*

Gavignet L, "Inhalateurs Buccaux", Annales Francaises Des Microtechniques Et De Chronometrie, Fr, vol. 47, 1998, pp. 95-96-121, the whole document.*

Gavignet, "Inhalateurs buccaux,"*Annales Francaises de Chronometrie et de Microtechnique* 47:95-96 (1998).

* cited by examiner

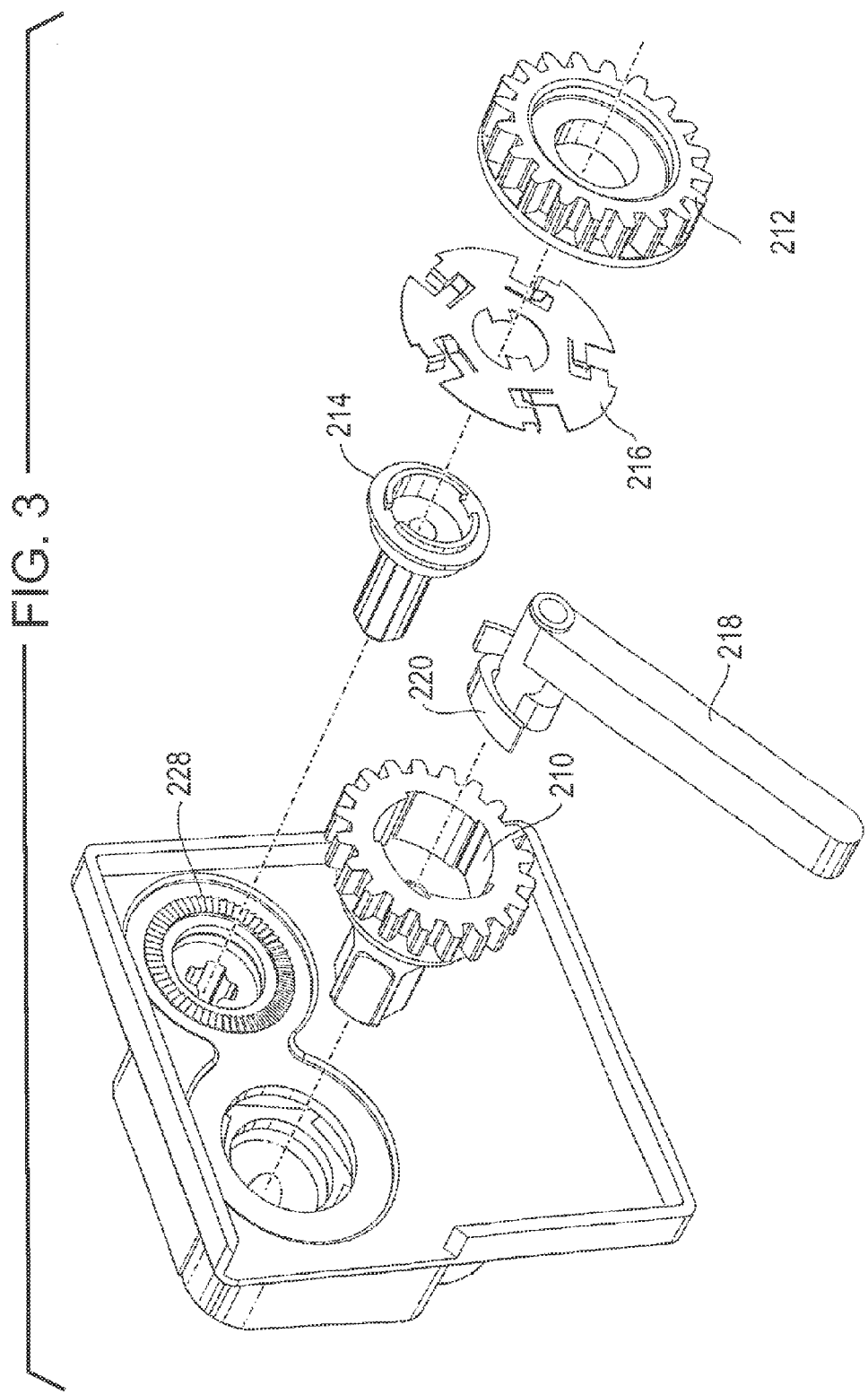

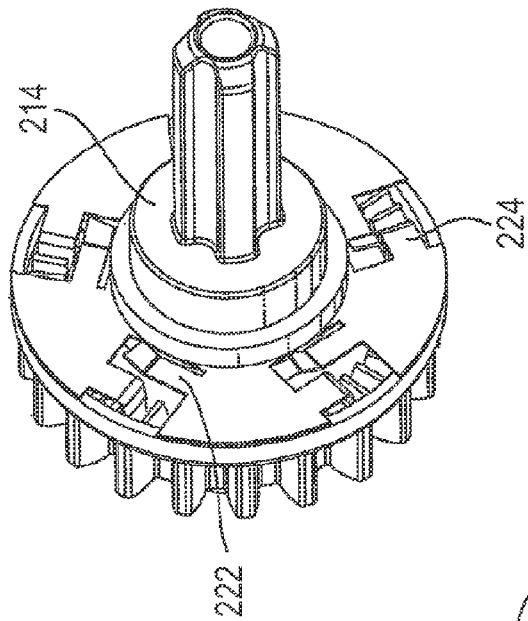
FIG. 4a
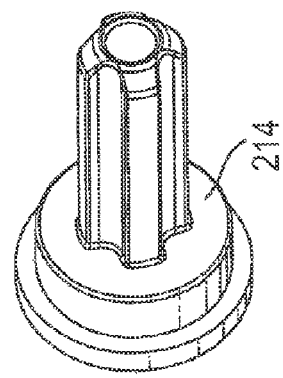
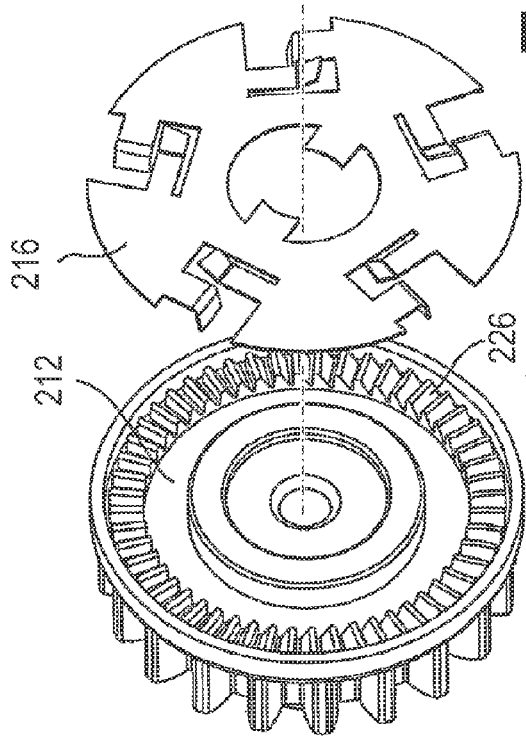
FIG. 4b

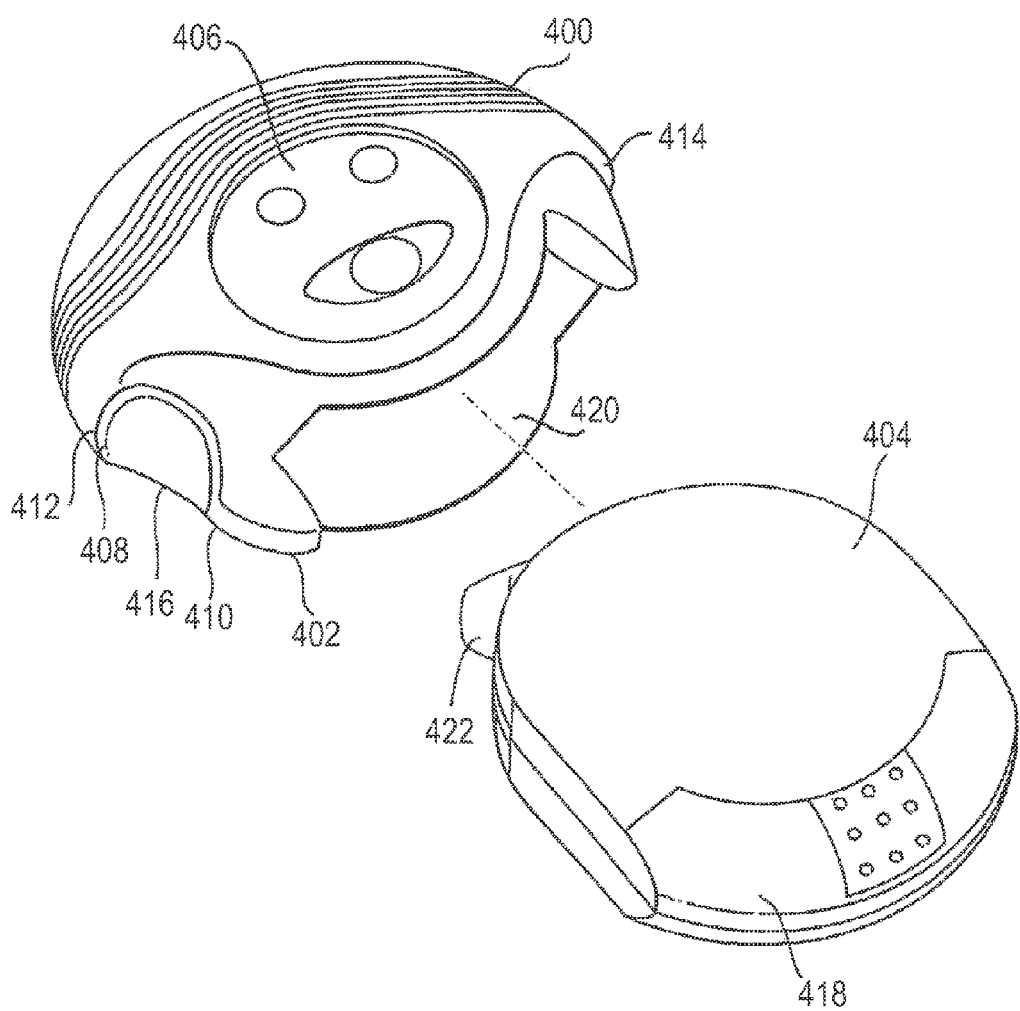

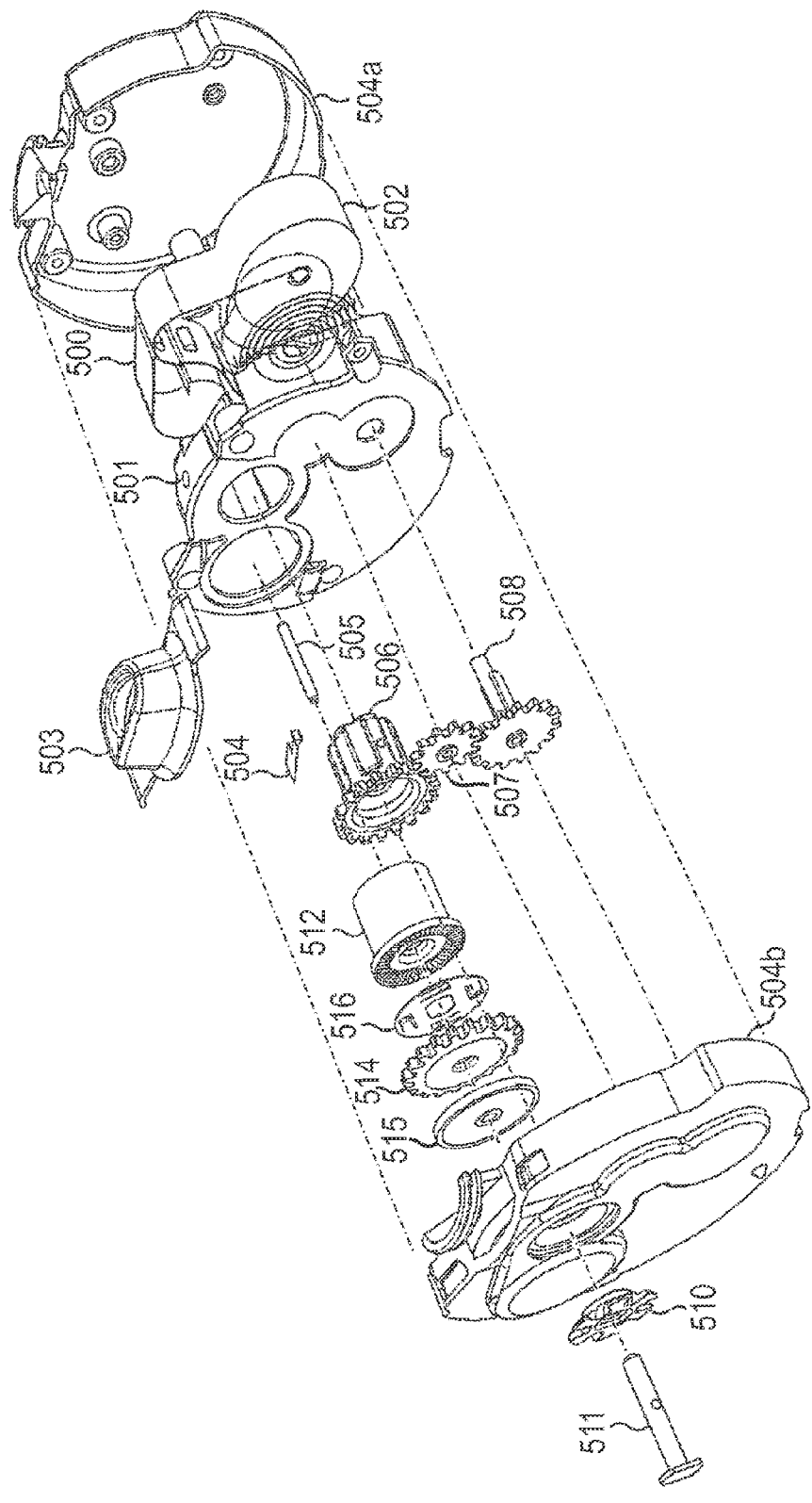

MEDICAMENT DISPENSER

This application is filed pursuant to 35 USC 371 as a United States National Phase Application of International Patent Application Serial No. PCT/EP02/11311 filed on 9 Oct. 2002, which claims priority from GB 0125134.7 filed on 19 Oct. 2001 in the United Kingdom.

TECHNICAL FIELD

The present invention relates to a medicament dispenser for dispensing medicament. The invention particularly relates to a device for use in dispensing medicament in powder or tablet form.

BACKGROUND TO THE INVENTION

The use of inhalation devices in the administration of medicaments, for example in bronchodilation therapy is well known. Such devices generally comprise a body or housing within which a medicament carrier is located. Known inhalation devices include those in which the medicament carrier is a blister strip containing a number of discrete doses of powdered medicament. Such devices usually contain a mechanism of accessing these doses, usually comprising either piercing means or means to peel a lid sheet away from a base sheet. The powdered medicament can then be accessed and inhaled. Such a mechanism may also be used for dispensing medicament in tablet form wherein peeling away the lid sheet from the base sheet reveals a tablet for removal and subsequent consumption.

It is an object of the present invention to simplify the internal mechanism of a medicament dispenser for dispensing medicament in powder or solid form from a medicament carrier as described supra.

Yet another object of the present invention is to provide a device which is refillable by insertion of a replacement cassette containing a medicament carrier. The cassette may be replaced when the medicament carrier is empty. The device is therefore more 'environmentally friendly' as the majority of the device may be retained and is not disposable. It also allows the device to be fitted with additional features such as electronics which may not be cost effective on a completely disposable device.

It is a further object of the present invention that the cassette may be easily removed and that a new replacement cassette can be easily inserted. It is also desirable that the operation of the medicament dispenser be straightforward and non-complex and in particular that the number of separate steps involved in preparing the device for use be minimised. This is especially relevant where the device is designed for use in the delivery of medicament in emergency or rescue situations (e.g. asthma attacks) where simplicity and ease of use is paramount.

When not in use it is desirable from a hygiene standpoint that a mouthpiece, or other medicament exit channel, is provided with some kind of protective cover. The cover desirably acts both to prevent build-up of dirt and to prevent ingress of dirt into the body of the device through the mouthpiece or channel, which might then be subject to inhalation or consumption by a patient. It is also desirable that the cover is in some way attached or mounted to the device to minimise the risk that the cover is misplaced or lost. It is therefore a further object of the present invention for the body of the device to act as a mouthpiece or exit channel cover when the device is in storage and that the cassette is movable relative to the body to enable the mouthpiece or channel to be uncovered for use by the patient.

It is a further object of the invention to provide a medicament dispenser device suitable for Use with a large number of discrete doses but which is of an acceptable size for use by patients.

SUMMARY OF THE INVENTION

Accordingly, in one aspect the invention provides medicament dispenser for use with a medicament carrier having a plurality of pockets for containing medicament wherein said pockets are spaced along the length of and defined between two peelable sheets secured to each other, said dispenser having an internal dispensing mechanism for accessing said medicament contained within said medicament carrier, said mechanism comprising, a) an opening station for receiving a pocket of said medicament carrier;

b) peeling means positioned to engage a base sheet and a lid sheet of a pocket which has been received in said opening station for peeling apart such a base sheet and lid sheet, to open such a pocket, said peeling means including lid driving means for pulling apart a lid sheet and a base sheet of a pocket that has been received at said opening station, said lid driving means comprising a wheel on which said lid sheet is wound, said wheel having an effective winding surface, the diameter of which increases as more lid sheet is wound about said wheel, c) an outlet, positioned to be in communication with an opened pocket through which a user can remove medicament from such an opened pocket;

d) indexing means for indexing in communication with said outlet, pockets of a medicament carrier in use with said medicament dispenser, said indexing means being interconnected with said lid driving means such that movement of one correlates with the movement of the other; and e) clutch means, in communication with the indexing means and the lid driving means, said clutch means comprising a gearing surface defining plural gear engagement positions; and plural gear teeth for engaging said plural gear engagement positions, wherein the plural gear teeth are arranged such that at any one time only a single gear tooth engages a single gear engagement position.

It will be appreciated that, in use, the clutch means acts to compensate for the increase in diameter of said effective winding surface of the lid driving means. The clutch means allows for slippage when the tension in the lid sheet is greater than the force required to peel apart the lid sheet and the base sheet.

It will be appreciated that in total, the clutch means effectively defines a number of individual gear positions which is greater than the number of gear engagement positions. This is therefore advantageous over a traditional slipping clutch arrangement comprising intermeshing gear wheels, where the effective number of individual gear positions defined is either equal to, or no more than, the number of gear engagement positions defined by one of the gear wheels. The clutch means herein is also typically more compact than traditional slipping clutch arrangements e.g. because it enables smaller gearing surfaces to be employed.

In a preferred aspect, the gearing surface and plural gear teeth are arranged such that the number of individual gear positions defined is equal to the number of gear engagement positions multiplied by the number of gear teeth. In one example, if the gearing surface defines 60 gear engagement positions and there are 6 gear teeth, then up to 360 individual gear positions are definable (e.g. 1° resolution on a rotating gear system).

Suitably, the gearing surface defines from 20 to 100, preferably from 40 to 80 gear engagement positions. Suitably, the number of gear teeth is from 2 to 20, preferably from 3 to 10.

In one aspect, the gear engagement positions are equally spaced (e.g. equidistantly spaced) and the gear teeth are offset (e.g. non-equidistantly spaced) relative thereto. Such offset arrangement maximises the number of effective individual gear positions which are capable of definition. An example of this aspect, is the Vernier spring arrangement described herein.

In another aspect, the gear engagement positions are also equally spaced (e.g. equidistantly spaced) and the gear teeth are located on a wobbling element capable of wobbling the gear teeth to plural offset (e.g. non-equidistantly spaced) positions. Such a wobbling offset arrangement also maximises the number of effective individual gear positions which are capable of being defined. An example of this aspect, is the wobbling wheel arrangement described herein.

In aspects, the clutch means is non-integral with either of the lid driving means or the indexing means, but forms a separate interconnecting component.

Suitably, the gearing surface comprises a gear wheel. As used herein, the term gear wheel encompasses, for example, a wheel, spindle or spool.

Suitably, the gear teeth may be arranged to be in ratchet form (i.e. enabling movement in one direction only).

Suitably, the gearing surface and gear teeth are in biased (e.g. sprung) engagement.

In one embodiment, said indexing means comprises a rotatable index wheel having recesses therein, said index wheel being engageable with a medicament carrier in use with said medicament dispenser such that said recesses each receive a respective pocket of the base sheet of a medicament carrier in use with said medicament dispenser.

Alternatively, said indexing means may comprise an indexing ratchet which is moveable between a locked position whereby said ratchet engages a pocket on said medicament carrier and prevents further peeling thereof, and a release position allowing free movement of said medicament carrier, and actuation of said medicament dispenser actuates said lid driving means and releases said index ratchet from said medicament carrier to allow peeling thereof.

Suitably, the medicament dispenser further comprises an indexing lever for actuating said dispenser wherein said indexing lever is interconnected with said indexing means and/or said lid driving means.

In one aspect, the lid driving means and/or the indexing means may be operated by an electronic drive system. The electronic drive system may also be used in conjunction with a mechanical drive system.

The electronic drive typically comprises a motor, preferably an electrically-powered motor. The motor may provide linear or rotary drive, but in general, rotary motors are most suitable. The motor may for example, comprise a DC electric motor, a piezoelectric (PZ) motor, an ultrasonic motor, a solenoid motor or a linear motor. Preferably, the electronic drive system comprises a DC motor, a PZ motor or an ultrasonic motor.

The use of ultrasonic motors is particularly preferred since they offer advantages over conventional motors in terms of weight, size, noise, cost and torque generated. Ultrasonic motors are well known in the art and are commercially available (e.g. BMSTU Technological Cooperation Centre Ltd, Moscow, Russia; Shinsei Corporation, Tokyo, Japan).

Ultrasonic motors do not use coils or magnets but comprise a piezo-electric ceramic stator which drives a coupled rotor. The stator generates ultrasonic vibrations which in turn causes rotation of the rotor. While regular DC motors are characterised by high speed and low torque, requiring reduction gearing to increase torque, ultrasonic motors attain low speed and high torque, thus eliminating the need for reduction gearing. Furthermore, these motors are lightweight and compact, lacking coils and magnets, and are noiseless as the ultrasonic frequencies used are not audible to the human ear.

Suitably, the dispenser further comprises actuating means for actuating said electronic drive system. Said actuating means may take the form of a switch, push-button, or lever.

In another aspect, the coil comprising the unused medicament strip may be surrounded by a constant force spring. Alternatively, the coil comprising the unused medicament strip may be surrounded by an elastomeric band or band comprising a contractible material. The constant force spring, elastomeric band or band comprising a contractible material contracts as the coil reduces in size.

Suitably, said peeling means additionally comprise a guide for guiding the lid sheet and base sheet along separate paths at the opening station. The lid sheet is passed around the guide portion onto the lid driving means.

Alternatively, the guide comprises a roller mechanism. The lid sheet is fed over the rollers onto the lid driving means.

Suitably, the internal mechanism additionally comprises a first chamber in which the strip is initially housed and from which it is dispensed and a second chamber to receive the used portion of the base sheet after it has been indexed and separated from the lid sheet.

Suitably, said first chamber and said second chamber are separated by a wall. Suitably, said wall is movable to adjust the size of said first and second chambers.

Alternatively, said wall is flexibly movable to adjust the size of the first and second chambers.

Alternatively, the second chamber is expandable to create space for the growing coil of the used portion of the base sheet.

Suitably, the internal mechanism further comprises a third chamber to receive the used portion of the lid sheet and a fourth chamber which houses the indexing means. The fourth chamber may communicate via a slit, which in turn extends upwardly within a mouthpiece or exit channel and communicates with air inlets.

Suitably, the internal mechanism additionally comprises a crushing wheel to crush the medicament pockets after the medicament has been removed from them. The crushing wheel therefore reduces the space, which the used portion of the base sheet takes up.

Typically, the internal mechanism for accessing said medicament contained within said medicament carrier is housed within a cassette.

Thus, in another embodiment, the invention provides a medicament dispenser for dispensing medicament comprising: a body; a holder, shaped to fit within said body and movable relative to said body; and receivable by said holder, said cassette containing said medicament carrier.

Suitably, movement of the holder relative to the body results in movement of the cassette between a first position and a second position such that the cassette is reversibly removable from the holder when the cassette is in the second position.

Suitably, the first position comprises a dispensing position. Preferably the second position comprises a non-dispensing position. The cassette is therefore only removable from the holder when the cassette is in the non-dispensing position.

Suitably, the holder and body include attaching means to attach the holder to the body. Preferably said attaching means comprise a snap fit mechanism.

Suitably, said snap fit mechanism comprises a pin and hole system.

Suitably, the holder is pivotally movable relative to the body.

Alternatively, the holder is rotationally movable relative to the body.

Suitably, the holder additionally comprises a stop to limit movement of the holder relative to the body. The stop abuts against the edge of the body at two points when it is rotated. At these points the holder may be designed to click into place. Therefore when the stop abuts one body edge then it is clicked into the dispensing position and when the stop abuts the other body edge then it is clicked into the non-dispensing position.

Alternatively, the holder is slidably movable relative to the body.

Suitably, the holder additionally comprises a catch to retain the cassette. The catch may for example comprise a sprung pin which fits into a hole or an integral catch which deforms when pressed allowing removal of the cassette.

Suitably, the catch is child resistant. Child resistance may be realised by having a system which forces the user to perform two actions at once to remove the cassette. Other features of the catch may include shock or impact resistance, the ability to lock the catch and orientation features to ensure that the cassette can only be inserted one way. The catch should also be easy to manufacture and assemble, be robust, be composed of a minimal number of components and intrude minimally into the space into which the cassette is inserted.

Suitably, the holder includes guide means to guide the cassette into the holder. Suitably, said guide means comprise guide rails. Alternatively the guide means comprise grooves, indentations or other shaping or surface details to define a 'lock and key' relationship between the holder and the cassette. Colour guides, arrows and any other surface markings may also be employed.

Suitably, the cassette additionally comprises an indexing lever. The indexing lever has a finger tab located outside the body of the cassette. The rest of the indexing lever is located within the cassette. The indexing lever may have teeth at its tail end and/or teeth along its mid portion.

Suitably, the cassette additionally comprises a mouthpiece.

Suitably, said mouthpiece is extendable. The mouthpiece extends as the cassette and holder are moved from the non-dispensing position to the dispensing position.

Alternatively, the mouthpiece is retractable. The mouthpiece retracts as the cassette and holder are moved from the dispensing position to the non-dispensing position.

In one aspect, the mouthpiece is telescopic. In another aspect, the mouthpiece is fixed.

The medicament dispenser may also be designed for nasal inhalation of a powdered medicament and may therefore incorporate a nosepiece as an alternative to a mouthpiece. If the medicament is in solid form, the dispenser may incorporate an exit channel for tablet release.

Suitably, the body covers the mouthpiece and indexing lever when the cassette is in the non-dispensing position. This avoids the need for a separate cover and protects the mouthpiece from the ingress of dirt and contaminants during storage.

Suitably, the cassette additionally comprises a raised portion to fit against the holder. The raised portion is located at the opposite end of the cassette to the mouthpiece/nosepiece/exit and indexing lever and prevents the incorrect insertion of the cassette into the holder since it is too wide to fit into the holder. The raised portion is shaped such that it fits against a cut away part of the holder. Suitably, said raised portion includes a section which is raised to define a grip portion.

Suitably, at least a portion of the holder and body are shaped for ease of grip by the user.

Suitably, operation of the device may be performed with one hand.

Suitably, the medicament dispenser comprises an actuation or dose counter for counting the number of actuations of the indexing lever or releases of dose from the cassette.

The dose counter may count the number of doses left to be taken or the number of doses taken.

Suitably, said dose counter is electronic. Alternatively, said dose counter is mechanical.

Suitably, said dose counter is located within the cassette. Alternatively, the dose counter is external to the cassette.

Alternatively the blister strip has printed numbers on it corresponding to the doses in the pockets. Suitably, said printed numbers are visible through a window in the cassette. The device may be assembled as follows. The holder is snap fitted into the body. The cassette is assembled separately. The body of the cassette is formed, preferably in two sections with any necessary spindles or integral components formed into the base. Individual components such as indexing wheels, lid, winding mechanisms, guide portions etc are then assembled into the base. Finally the medicament containing blister strip (or other suitable medicament carrier) may be inserted into the cassette. This may be wound into the device before the lid is attached to the cassette and the cassette sealed. Alternatively, the cassette may be formed completely apart from a hole left in its side for insertion of the blister strip or medicament carrier. The hole may then be sealed to complete the cassette. This second method of inserting the medicament carrier into the device has the advantage that it is much simpler.

Suitably, the medicament dispenser additionally comprises an electronic data management system. The electronic data management system has input/output capability and comprises a memory for storage of data; a microprocessor for performing operations on said data; and a transmitter for transmitting a signal relating to the data or the outcome of an operation on the data.

Suitably, the electronic data management system is arranged to be responsive to or activated by the voice of a user. Thus, for example the system may be switched on or off in response to a voice command.

The electronic data management system may be integral with the body. Alternatively, the electronic data management system forms part of a base unit which is reversibly associable with the body.

Suitably, the medicament dispenser additionally comprises a data input system for user input of data to the electronic data management system. Preferably, the data input system comprises a man machine interface (MMI) preferably selected from a keypad, voice recognition interface, graphical user interface (GUI) or biometrics interface.

Energy may be conserved by a variety of means to enable the device to operate for longer on a given source of energy, such as a battery. Energy conservation or saving methods have additional advantages in terms of reducing the size requirements of the power source (e.g. battery) and thus the weight and portability of the medicament dispenser.

A variety of energy saving methods are available which generally involve reducing power consumption. One such method is to use a clock or timer circuit to switch the power on and off at regular or predetermined intervals. In another method the system can selectively switch on/off specific electronic devices, such as visual display units or sensors, in order to power these devices only when they are required to perform a particular sequence of events. Thus different electronic devices may be switched on and off at varying intervals and for varying periods under control of the system. The power sequencing system may also respond to a sensor, such as a motion or breath sensor, which is activated on use of the device.

Low power or "micropower" components should be used within the electronics where possible and if a high power device is required for a particular function this should be put into a low power standby mode or switched off when not required. Similar considerations apply in the selection of transducers. Operation at low voltage is desirable since power dissipation generally increases with voltage.

For low power digital applications complementary metal oxide semi-conductor (CMOS) devices are generally preferred and these may be specially selected by screening for low quiescent currents. Clock speeds of processors and other logic circuits should be reduced to the minimum required for computational throughput as power consumption increases with frequency. Supply voltages should also be kept at minimal values consistent with reliable operation because power dissipation in charging internal capacitance's during switching is proportional to the square of the voltage. Where possible, supply voltages should be approximately the same throughout the circuit to prevent current flowing through input protection circuits. Logic inputs should not be left floating and circuits should be arranged so that power consumption is minimised in the most usual logic output state. Slow logic transitions are undesirable because they can result in relatively large class A currents flowing. Resistors may be incorporated in the power supply to individual devices in order to minimise current in the event of failure.

In some control applications, devices that switch between on and off states are preferred to those that allow analog (e.g. linear) control because less power is dissipated in low resistance on states and low current off states. Where linear components are used (e.g. certain types of voltage regulators) then types with low quiescent currents should be selected. In some circuit configurations it is preferable to use appropriate reactive components (i.e. inductors and capacitors) to reduce power dissipation in resistive components.

Suitably, the system additionally comprises a visual display unit for display of data from the electronic data management system to the user. The display may for example, comprise a screen such as an LED or LCD screen. More preferably the visual display unit is associable with the body of the medicament dispenser.

Suitably, the medicament dispenser additionally comprises a datalink for linking to a local data store to enable communication of data between the local data store and the electronic data management system. The datastore may also comprise data management, data analysis and data communication capability.

The datastore may itself form part of a portable device (e.g. a handheld device) or it may be sized and shaped to be accommodated within the patient's home. The datastore may also comprise a physical storage area for storage of replacement cassettes. The datastore may further comprise a system for refilling medicament from a reservoir of medicament product stored therewithin. The datastore may further comprise an electrical recharging system for recharging any electrical energy store on the medicament dispenser, particularly a battery recharging system.

The datalink may for example enable linking with a docking station, a personal computer, a network computer system or a set-top box by any suitable method including a hardwired link, an infrared link or any other suitable wireless communications link.

Suitably, the medicament dispenser additionally comprises an actuation detector for detecting actuation of the dispensing mechanism wherein said actuation detector transmits actuation data to the electronic data management system.

The medicament dispenser may additionally comprise a safety mechanism to prevent unintended multiple actuations of the dispensing mechanism. The patient is thereby protected from inadvertently receiving multiple doses of medicament in a situation where they take a number of short rapid breaths. More preferably, the safety mechanism imposes a time delay between successive actuations of the release means. The time delay is typically of the order of from three to thirty seconds.

Suitably, the medicament dispenser additionally comprises a release detector for detecting release of medicament from the cassette, wherein said release detector transmits release data to the electronic data management system.

Suitably, the medicament dispenser additionally comprises a shake detector for detecting shaking of the medicament container (e.g. prior to actuation of the dispensing mechanism), wherein said shake detector transmits shake data to the electronic data management system.

Suitably, any actuation detector, release detector, or shake detector comprises a sensor for detecting any suitable parameter such as movement. Any suitable sensors are envisaged including the use of optical sensors. The release detector may sense any parameter affected by release of the medicament such as pressure, temperature, sound, moisture, carbon dioxide concentration and oxygen concentration.

Suitably, the medicament dispenser additionally comprises a breath trigger for triggering the dispensing mechanism, said breath trigger being actuable in response to a trigger signal from the electronic data management system. Preferably, the electronic data management system includes a predictive algorithm or look-up table for deriving from the breath data when to transmit the trigger signal. For example, a real-time analysis of the patient breath waveform may be made and the trigger point derived by reference to that analysed waveform.

Suitably, the electronic data management system includes a predictive algorithm or look-up table for calculating the optimum amount of medicament to dispense.

Suitably, the memory on the electronic data management system includes a dose memory for storing dosage data and reference is made to the dose memory in calculating the optimum amount of medicament to dispense.

Suitably, the medicament dispenser additionally comprises a selector for selecting the amount of medicament to dispense from said dispensing mechanism. In one aspect, the selector is manually operable. In another aspect, the selector is operable in response to a signal from the transmitter on the electronic data management system.

Suitably, the medicament dispenser comprises in association with a body or housing thereof, a first transceiver for transmitting and receiving data and in association with the medicament container, a second transceiver for transmitting and receiving data, wherein data is transferable in two-way fashion, from the first transceiver to the second transceiver.

The data is preferably in digital form and suitable for transfer by electronic on optical means. An medicament dispenser of this general type is described in pending UK Patent Application No. 0020538.5.

One advantage of embodiments of this type is the ability to store many types of information in different parts of the memory structure of the transceivers. The information is furthermore stored in a form which is readily and accurately transferable. The information could for example, include manufacturing and distribution compliance information written to the memory at various points in the manufacturing or distribution process, thereby providing a detailed and readily accessible product history of the dispenser. Such product history information may, for example, be referred to in the event of a product recall. The compliance information could, for example, include date and time stamps. The information could also include a unique serial number stored in encrypted form or in a password protectable part of the memory which uniquely identifies the product and therefore may assist in the detection and prevention of counterfeiting. The information could also include basic product information such as the nature of the medicament and dosing information, customer information such as the name of the intended customer, and distribution information such as the intended product destination.

On loading or reloading the medicament dispenser with a cassette the second transceiver may, for example, read the unique serial number, batch code and expiry date of the medicament and any other information on the second transceiver. In this way the nature and concentration of the medicament, together with the number of doses used or remaining within the cassette, may be determined. This information can be displayed to the patient on a visual display unit. Other information, such as the number of times the medicament dispenser has been reloaded with a cassette, may also be displayed.

Similarly, should the cassette be removed from the holder before the supply of medicament is exhausted, the same data can be read from the second transceiver and the number of doses remaining or used determined. Other information, such as the date and time of administration of the drug, or environmental exposure data such as the minimum/maximum temperatures or levels of humidity the cassette has been exposed to, may also be read and displayed to the user.

In the event that the supply of medicament within the container becomes exhausted, or that the shelf life of the medicament has expired, or that the first transceiver does not recognise the batch code on the second transceiver, activation of the dispenser may be prevented to safeguard the user. Activation may also be prevented if the medicament has been exposed to extreme environmental conditions for periods outwith the manufacturer's guidelines.

Data may be transferred to and from any transceiver during the period of use of the medicament dispenser by the patient. For example, the medicament dispenser may include an electronic data management system having various sensors associated therewith. Any data collected by the sensors or from any data collection system associated with the electronic data management system including a clock or other date/time recorder is transferable.

Data may be transferred each time the patient uses the device. Or alternatively, data may be stored in a database memory of the electronic data management system and periodically downloaded to any transceiver. In either case, a history of the usage of the device may be built up in the memory of a transceiver.

In one embodiment herein, a history of the usage of the medicament dispenser is transferred to the second transceiver. When the blister strip in the cassette is exhausted it is exchanged by the patient for a new refill cassette. At the point of exchange, which will typically occur at the pharmacy, data may be transferred from the exhausted cassette to the refill and vice-versa. Additionally, usage history data may be read from the refill and transferred to a healthcare data management system for example comprising a network computer system under the control of a healthcare data manager.

Methods are envisaged herein-whereby the patient is given some sort of reward for returning the refill and making available the data comprised within the second transceiver. Methods are also envisaged herein whereby the healthcare data manager is charged for either receipt of the data from the second transceiver or for its use for commercial purposes. Any rewards or charging may be arranged electronically. The methods may be enabled by distributed or web-based computer network systems in which any collected data is accessible through a hub on the network. The hub may incorporate various security features to ensure patient confidentiality and to allow selective access to information collected dependent upon level of authorisation. The level of user authorisation may be allocated primarily to safeguard patient confidentiality. Beyond this the level of user authorisation may also be allocated on commercial terms with for example broader access to the database being authorised in return for larger commercial payments.

Suitably, the first and second transceiver each comprise an antenna or equivalent for transmitting or receiving data and connecting thereto a memory. The memory will typically comprise an integrated circuit chip. Either transceiver may be configured to have a memory structure which allows for large amounts of information to be stored thereon. The memory structure can be arranged such that parts of the memory are read-only, being programmed during/after manufacture, other parts are read/write and further parts are password protectable. Initial transfer of information (e.g. on manufacture or one dispensing) to or from any transceiver can be arranged to be readily achievable by the use of a reader which is remote from the medicament dispenser, thereby minimising the need for direct product handling. In further aspects, the reader can be arranged to simultaneously read or write to the memory of multiple transceivers on multiple medicament dispensers.

A suitable power source such as a battery, clockwork energy store, solar cell, fuel cell or kinetics-driven cell will be provided as required to any electronic component herein. The power source may be arranged to be rechargeable or reloadable.

Suitably, data is transferable in two-way fashion between the first and second transceiver without the need for direct physical contact therebetween. Preferably, data is transferable wirelessly between the first and second transceiver.

Suitably, the first transceiver is an active transceiver and the second transceiver is a passive transceiver. The term active is used to mean directly-powered and the term passive is used to mean indirectly-powered.

Suitably, the second transceiver comprises a label or tag comprising an antenna for transmitting or receiving energy; and an integrated circuit chip connecting with said antenna, and the first transceiver comprises a reader for said label or tag. In this case the label or tag is a passive transceiver and the reader is an active transceiver. Preferably, the reader will not need to be in direct contact with the tag or label to enable the tag or label to be read.

The tag may be used in combination and/or integrated with other traditional product labelling methods including visual text, machine-readable text, bar codes and dot codes.

Suitably, the integrated circuit chip has a read only memory area, a write only memory area, a read/write memory area or combinations thereof.

Suitably, the integrated circuit chip has a one-time programmable memory area. More preferably, the one-time programmable memory area contains a unique serial number.

Suitably, the integrated circuit chip has a preset memory area containing a factory preset, non-changeable, unique data item. The preset memory item is most preferably in encrypted form.

Suitably, the integrated circuit chip has plural memory areas thereon. Suitably, any memory area is password protected.

Suitably, any memory area contains data in encrypted form. Electronic methods of checking identity, error detection and data transfer may also be employed.

In one aspect, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

Suitably, the tag is on a carrier and the carrier is mountable on the body or holder of the medicament dispenser or on the cassette.

In one aspect, the carrier is a flexible label. In another aspect, the carrier is a rigid disc. In a further aspect, the carrier is a rectangular block. In a further aspect, the carrier is a collar ring suitable for mounting to the neck of an aerosol container. Other shapes of carrier are also envisaged.

Suitably, the carrier is mouldable or weldable to the cassette or housing. Suitably, the carrier encases the tag. More preferably, the carrier forms a hermetic seal for the tag.

In one aspect, the carrier comprises an insulating material such as a glass material or, a paper material or an organic polymeric material such as polypropylene. Alternatively, the carrier comprises a ferrite material.

The energy may be in any suitable form including ultrasonic, infrared, radiofrequency, magnetic, optical and laser form. Any suitable channels may be used to channel the energy including fibre optic channels.

In one aspect, the second transceiver comprises a radiofrequency identifier comprising an antenna for transmitting or receiving radiofrequency energy; and an integrated circuit chip connecting with said antenna, and the first transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or label to be read.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

Suitably, the antenna of the RFID tag is capable of transmitting or receiving radiofrequency energy having a frequency of from 100 kHz to 2.5 GHz. Preferred operating frequencies are selected from 125 kHz, 13.56 MHz and 2.4 GHz.

In one aspect, the second transceiver comprises a magnetic label or tag comprising an antenna for transmitting or receiving magnetic field energy; and an integrated circuit chip connecting with said antenna, and the first transceiver comprises a reader for said magnetic label or tag. In this case the magnetic label or tag is a passive transceiver and the reader is an active transceiver.

A suitable magnetic label or tag comprises plural magnetic elements in mutual association whereby the magnetic elements move relative to each other in response to an interrogating magnetic field. A magnetic label or tag of this type is described in U.S. Pat. No. 4,940,966. Another suitable magnetic label or tag comprises a magnetorestrictive element which is readable by application of an interrogating alternating magnetic field in the presence of a magnetic bias field which results in resonance of the magnetorestrictive elements at different predetermined frequencies. A magnetic label of this type is described in PCT Patent Application No. WO92/12402. Another suitable magnetic label or tag comprising plural discrete magnetically active regions in a linear array is described in PCT Patent Application No. WO96/31790. Suitable magnetic labels and tags include those making use of Programmable Magnetic Resonance (PMR) (trade name) technology.

In another aspect, the second transceiver comprises a microelectronic memory chip and the first transceiver comprises a reader for said microelectronic memory chip. The microelectronic memory chip may comprise an Electrically Erasable Programmable Read Only Memory (EEPROM) chip or a SIM card-type memory chip. In this case the microelectronic memory chip is a passive transceiver and the reader is an active transceiver.

Any transceiver herein, particularly a passive transceiver may be mounted on or encased within any suitable inert carrier. The carrier may comprise a flexible sheet which may in embodiments be capable of receiving printed text thereon.

In one aspect, the first transceiver is integral with the body such that a single unit is comprised. The first transceiver may for example be encased within or moulded to the body.

In another aspect, the first transceiver forms part of a base unit which is reversibly associable with the body. The base unit may for example, form a module receivable by the body such as a snap-in module.

Suitably, the medicament dispenser additionally comprises a communicator for wireless communication with a network computer system to enable transfer of data between the network computer system and the electronic data management system. Dispensers employing such communicators are described in pending PCT Applications Nos. PCT/EP00/09291 (PG3786), PCT/EP00/09293 (PG4029) and PCT/EP00/09292 (PG4159). Preferably, the communicator enables two-way transfer of data between the network computer system and the electronic data management system.

Suitably, the data is communicable between the network computer system and the electronic data management system in encrypted form. All suitable methods of encryption or partial encryption are envisaged. Password protection may also be employed. Suitably, the communicator employs radiofrequency or optical signals.

In one aspect, the communicator communicates via a gateway to the network computer system. In another aspect, the communicator includes a network server (e.g. a web server) such that it may directly communicate with the network.

In a further aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

In one aspect, the network computer system comprises a public access network computer system. The Internet is one suitable example of a public access network computer system, wherein the point of access thereto can be any suitable entrypoint including an entrypoint managed by an Internet service provider. The public access network computer system may also form part of a telecommunications system, which may itself be either a traditional copper wire system, a cellular system or an optical network.

In another aspect, the network computer system comprises a private access network computer system. The private access network system may for example, comprise an Intranet or Extranet which may for example, be maintained by a health service provider or medicament manufacturer. The network may for example include password protection; a firewall; and suitable encryption means.

Preferably, the communicator enables communication with a user-specific network address in the network computer system.

The user-specific network address may be selected from the group consisting of a web-site address, an e-mail address and a file transfer protocol address. Preferably, the user-specific network address is accessible to a remote information source such that information from said remote information source can be made available thereto. More preferably, information from the user-specific network address can be made available to the remote information source.

In one aspect, the remote information source is a medicament prescriber, for example a doctors practice. Information transferred from the medicament prescriber may thus, comprise changes to prescription details, automatic prescription updates or training information. Information transferred to the medicament prescriber may comprise compliance information, that is to say information relating to the patient's compliance with a set prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

In another aspect, the remote information source is a pharmacy. Information transferred from the pharmacy may thus, comprise information relating to the medicament product. Information sent to the pharmacy may thus include prescription requests which have been remotely pre-authorised by the medicament prescriber.

In a further aspect, the remote information source is an emergency assistance provider, for example a hospital accident and emergency service or an emergency helpline or switchboard. The information may thus, comprise a distress or emergency assist signal which requests emergency assistance.

In a further aspect, the remote information source is a manufacturer of medicament or medicament delivery systems. Information transferred to the system may thus, comprise product update information. The system may also be configured to feed information back to the manufacturer relating to system performance.

In a further aspect, the remote information source is a research establishment. In a clinical trial situation, information may thus be transferred relating to the trial protocol and information relating to patient compliance fed back to the research establishment.

In a further aspect, the remote information source is an environmental monitoring station. Information relating to weather, pollen counts and pollution levels may thus be made accessible to the system.

Suitably, the medicament dispenser additionally comprises a geographic positioning system such as a global positioning system or a system which relies on the use of multiple communications signals and a triangulation algorithm.

The medicament may comprise a capsule, pellet or tablet. Alternatively, the medicament may be in powdered form. Preferably, when in powdered form the medicament comprises a drug. Preferably the drug is selected from the group consisting of albuterol, salmeterol, fluticasone propionate and beclomethasone dipropionate and salts or solvates thereof and any combination thereof. Preferably said combination comprises salmeterol xinafoate and fluticasone propionate.

Suitably, the powdered medicament additionally comprises an excipient. Suitably, said excipient is a sugar.

In yet another aspect, the invention provides a kit of parts comprising a cassette as described supra, a holder for a cassette and a body wherein the holder is shaped to fit within said body and may be movable relative to said body.

In a further aspect, the invention provides a body and holder for use in the medicament dispenser described supra.

In still a further aspect, the invention provides a cassette for use in the medicament dispenser described supra.

In yet another aspect, the invention provides the use of a medicament dispenser as described supra.

BRIEF DESCRIPTION OF THE DRAWINGS

The invention will now be described with reference to the accompanying drawings in which:

FIG. 2b shows the other side of the base unit illustrated in FIG. 2a;

FIG. 3 shows an exploded view of the components of the base unit as shown in FIG. 2b;

FIG. 4a shows an enlarged view of a lid foil haul off wheel, Vernier spring and Vernier wheel in accordance with one aspect of the invention;

FIG. 4b shows an exploded view of the lid foil haul off wheel, Vernier spring and Vernier wheel as shown in FIG. 4a;

FIG. 8 shows a perspective view of a medicament dispenser according to the invention with the cassette removed from the holder and the body;

FIGS. 9a and 9b respectively show exploded views of the cassette and body/holder of a refillable medicament dispenser in accord with the present invention.

DETAILED DESCRIPTION OF THE DRAWINGS

Figure 1:
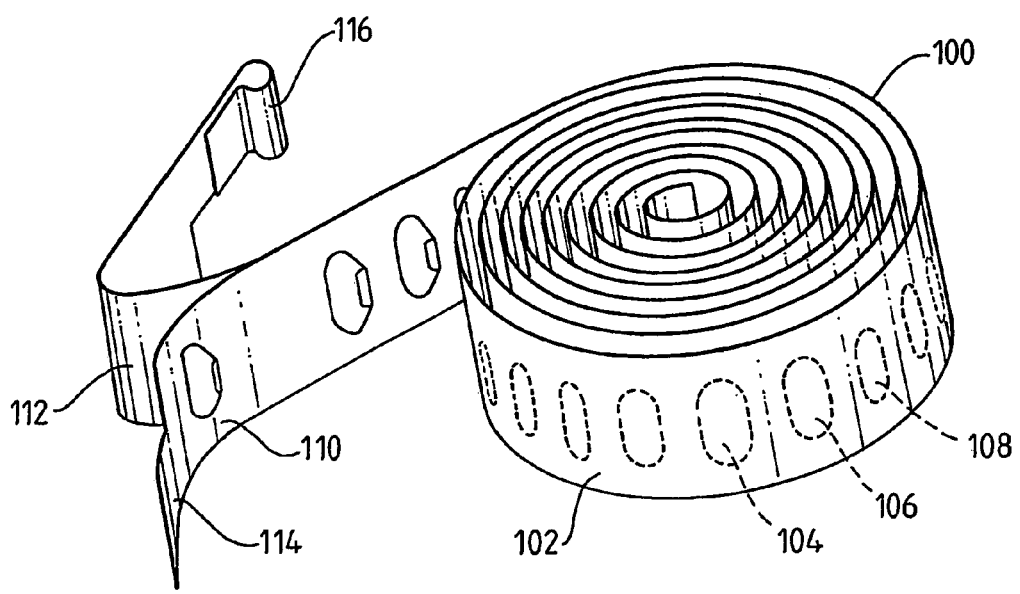
FIG. 1 shows a perspective view of a medicament carrier in accordance with the present invention.

Referring now to the Figures, FIG. 1 shows a medicament carrier 100 in accord with the present invention. The medicament carrier comprises a flexible strip 102 defining a plurality of pockets 104, 106, 108 each of which contains a dose of medicament which can be inhaled, in the form of powder.

The strip comprises a base sheet 110 in which blisters are formed to define the pockets 104, 106, 108 and a lid sheet 112 which is hermetically sealed to the base sheet except in the region of the blisters in such a manner that the lid sheet 112 and the base sheet 110 can be peeled apart. The sheets 110, 112 are sealed to one another over their whole width except for the leading end portions 114, 116 where they are preferably not sealed to one another at all. The lid 112 and base 110 sheets are each preferably formed of a plastics/aluminium laminate and are preferably adhered to one another by heat sealing.

The strip 102 is shown as having elongate pockets 104, 106, 108 which run transversely with respect to the length of the strip 102. This is convenient in that it enables a large number of pockets 104, 106, 108 to be provided in a given strip 102 length. The strip 102 may, for example, be provided with sixty or one hundred pockets but it will be understood that the strip 102 may have any suitable number of pockets.

Figure 2A:
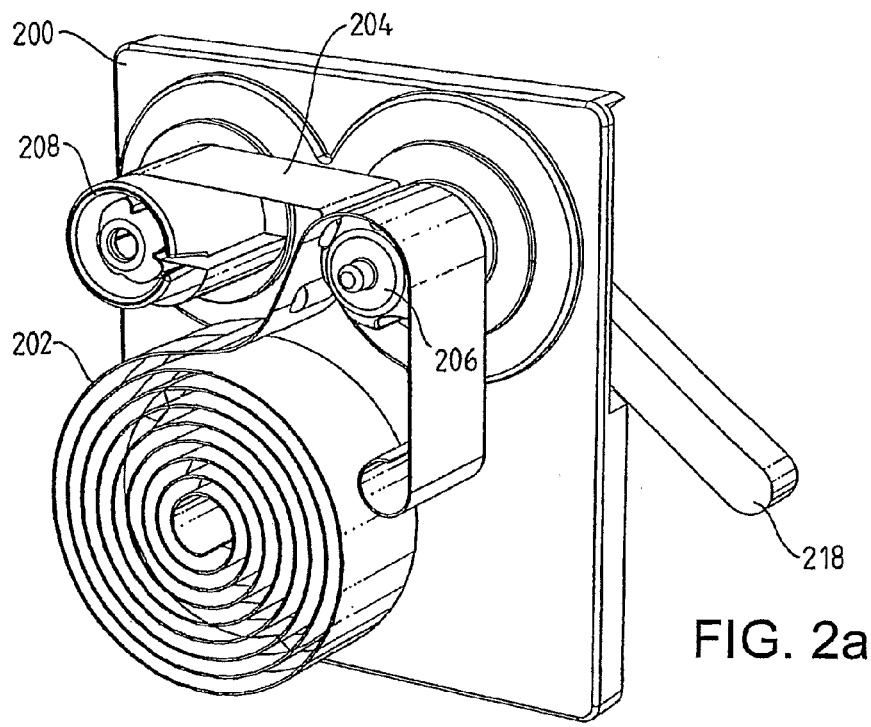
FIG. 2a shows one side of a base unit housing part of an internal mechanism in accordance with one aspect of the invention.
Figure 2B:
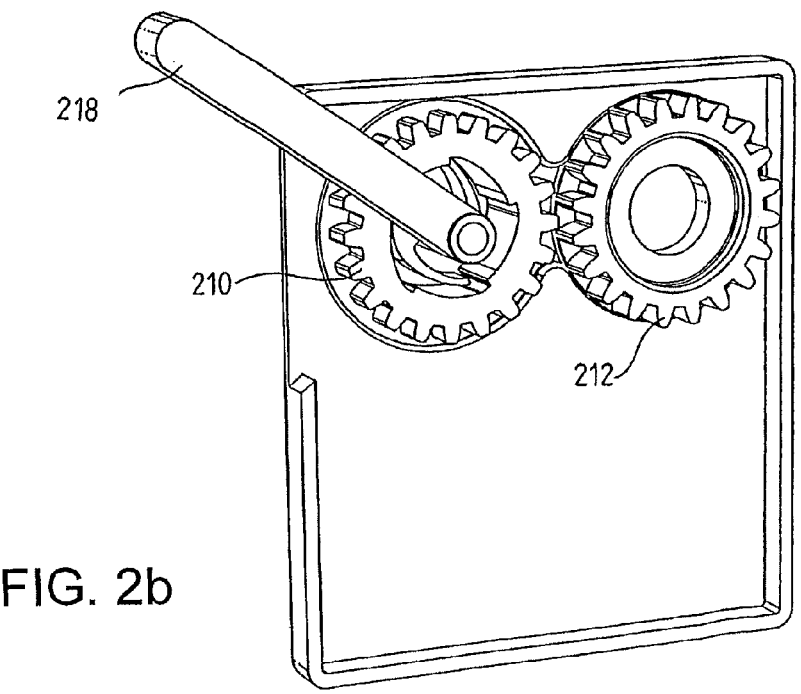

FIGS. 2a and 2b illustrates a base unit 200 in accordance with one aspect of the invention. The medicament carrier strip 202 and lid foil 204 are positioned on disposable by wheels. The index wheel 206 is a five pocket wheel and the foil wheel 208 is a fixed diameter cylinder. The lid foil 204 is positioned on the cylinder 208 by passing the foil tail into a slot and winding the wheel to tighten the foil onto it. The assembly is enclosed between two cassette halves (not shown). Ratchets and lock locations (not shown for clarity) are provided on the two wheels so that their position is fixed after assembly and cannot be altered until the cassette is securely installed in a base unit, and so the cassette can be removed and reassembled during use without losing the lid foil and medicament carrier strip positions.

The base unit has drive wheels 210, 212 which engage directly with the index and foil haul off wheels. In this example, the base unit comprises the following components; a base unit front cover 200, an index wheel drive spindle 210, a foil haul off drive wheel 214, a Vernier spring 216, a Vernier drive wheel 212 and a lever and ratchet 218.

The index wheel 210 advances one fifth of a turn for each full travel of the lever 218. The ratchet arms 220 on the lever can not reverse the movement of the index wheel drive spindle 210. The resulting rotary motion of the index wheel drive spindle 210 is delivered as a reciprocating action to the foil haul off assembly 212, 214, 216. Using the rotary motion of the index wheel drive spindle 210 rather than the movement of the actuating lever directly, disconnects the foil haul off wheel 214 from random movements of the actuating lever 218 and ensures it is driven in phase with the index wheel drive.

Each one fifth of a turn of the index wheel 210 delivers one fifth of a turn to the Vernier drive wheel 212.

Each one fifth rotation of the index wheel 210 has been translated into a reciprocating one fifth of a revolution of the Vernier drive wheel 212; the forward motion of the Vernier drive wheel 212 drives the Vernier spring 216. The Vernier spring 216 is designed to allow the foil haul off wheel 214 to run more slowly than the index wheel (necessary as the foil winds onto the wheel and the diameter of the effecting winding surface increases), and to resolve the difference in the amount of rotation of the two wheels sufficiently accurately for the foil advance action to be smooth, consistent and reliable.

The Vernier spring 216 has two sets of teeth; an inner set 222 and an outer set 224. The spring 216 is located by dog teeth 226 on the foil haul off drive wheel 212. The outer set of teeth 224 (outer to give the lowest tooth loads) engage the dog teeth 226 on the Vernier drive wheel 212 and transmit the peel torque to the foil haul off drive wheel 214. There are, for example, 61 teeth on the wheel 212 and five teeth on the Vernier spring 216; the teeth on the spring 216 engage one tooth at a time on the wheel 212, giving a possible 305 positions and a resolution of just over 1 (equivalent to just over 0.1 mm of foil travel).

There is a similar Vernier resolution between the inner set of teeth 222 on the spring 216 and the back face of the base unit case which comprises another set of dog teeth 228. When the lever 218 advances from its start position, the lever ratchet 220 engages with the index drive wheel 210 and rotates it. The Vernier wheel 212 is driven and engages with the Vernier spring 216 which is directly connected to the foil haul off drive wheel 214. The foil haul off wheel 214 rotates, peeling foil as the index wheel 210 advances. The foil haul off wheel 214 will be trying to peel foil faster than the index wheel 210 can deliver it (by up to 20% depending on the number of turns of foil on the haul off wheel); therefore the tension in the lid foil will increase. The Vernier spring 216 is designed such that it slips in relation to the Vernier wheel 212 within a predetermined torque range. The range is determined by the spring loads and the ratchet angles. The lowest torque value is higher than the torque required to peel the strip and lower than the torque that will break the strip. If torque is plotted against angle of slip between the two wheels, it will cycle over the Vernier pitch of approximately 1.

Figure 5:
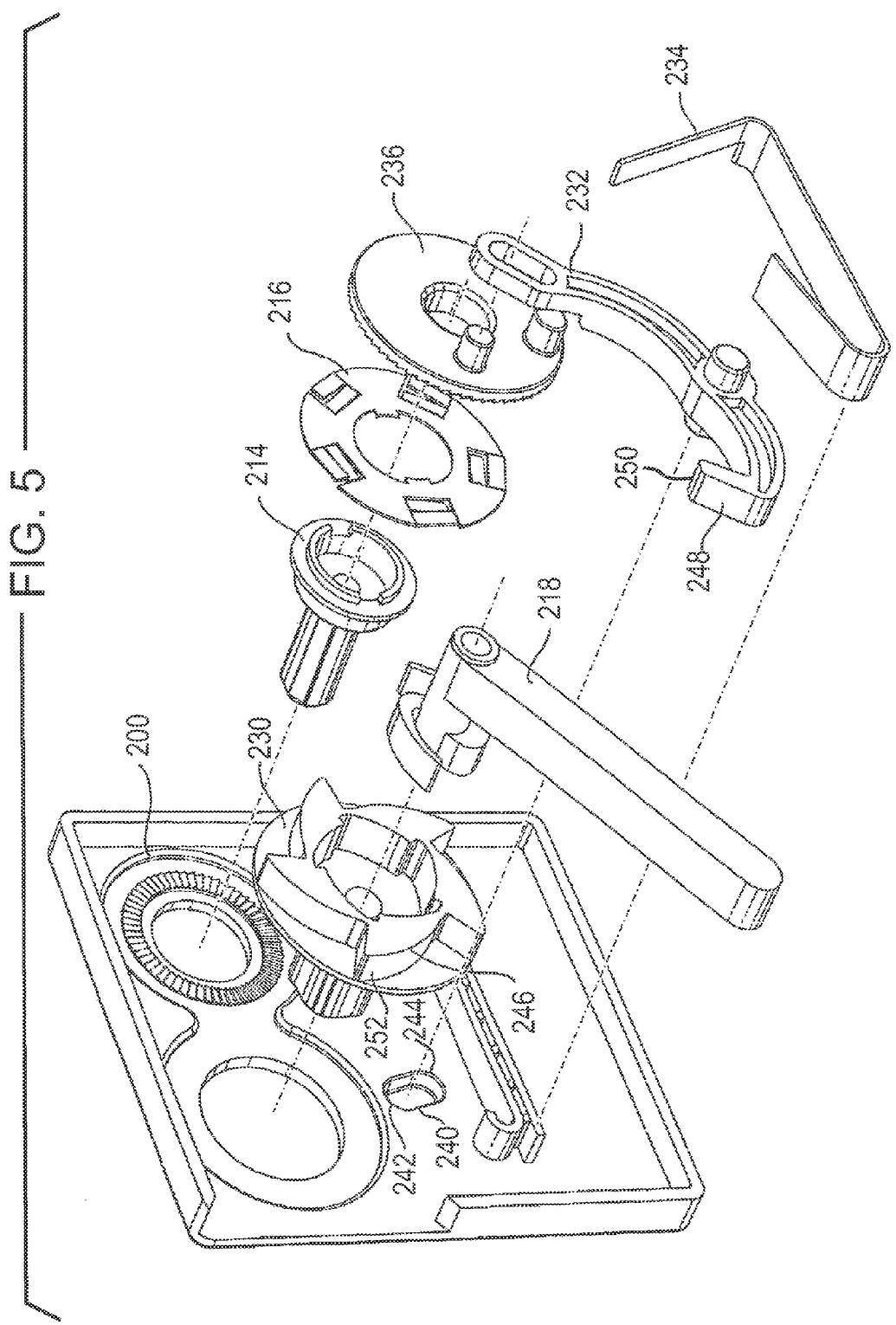
FIG. 5 shows an exploded view of the constituent components of the internal mechanism according to another aspect of the invention.

FIG. 5 shows an alternative assembly of components in accordance with another aspect of the invention. In this case a crank 232, overload/return spring 234 and an alternative Vernier drive wheel 236 are shown.

Figure 6A:
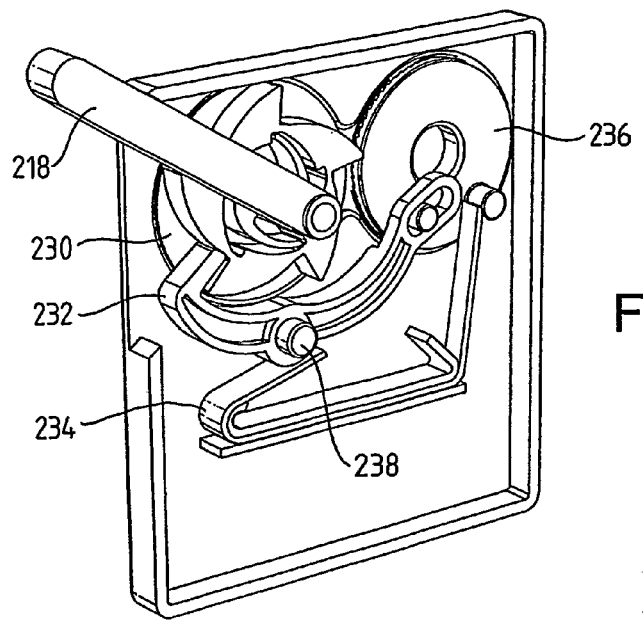
FIG. 6a shows the assembled components of FIG. 5 in a start position.
Figure 6B:
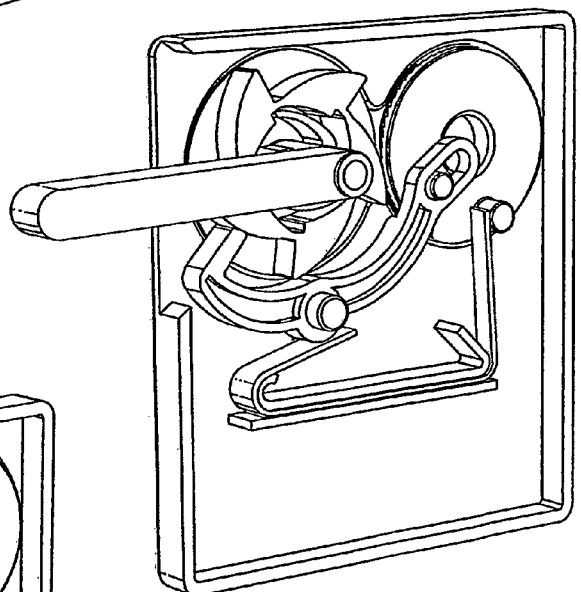
FIG. 6b shows the assembled components of FIG. 6a half way through an actuation cycle.
Figure 6C:
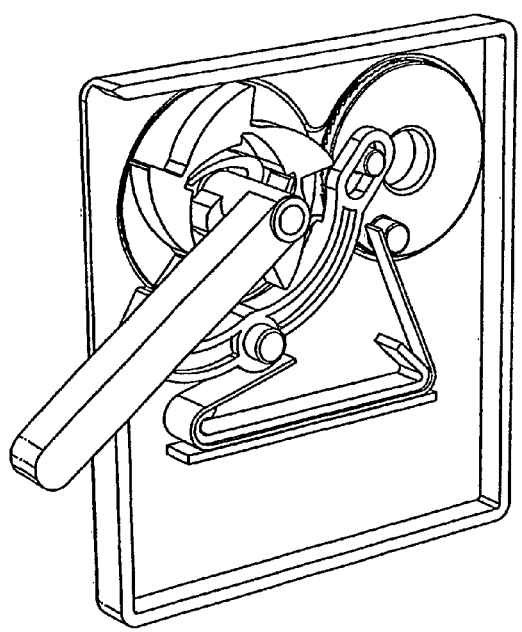
FIG. 6c shows the assembled components of FIGS. 6a and 6b at full actuation.

As shown in FIGS. 6a to 6c, movement of the lever causes rotation of the index wheel 230. The resulting rotary motion of the index wheel drive spindle 230 is delivered as a reciprocating action to the foil haul off assembly by the cam profile 246 on the index wheel 230 and the cam profile 248 on the crank 232. Once again, each one fifth of a turn of the index wheel 230 delivers a one fifth of a turn to the Vernier drive wheel 236; once the crank nose 250 passes the end of an index wheel cam tooth 252, the return spring 234 pushes the Vernier drive wheel 236 and the crank 232 back to the start position. The returned crank 232 prevents the index wheel 230 reversing, gives a clear mechanical output and re-initialises the Vernier drive wheel 236.

At the start position as shown in FIG. 6a, the crank pivot 238 is sited at the upper section 242 of slot 240; the spring preload holds the crank 232 in place. The pivot point 238 of the crank 232 can move in slot 240 between point 242 and 244. This enables the index wheel 230 to move without rotating the foil haul off wheel 214 or the Vernier wheel 236. The strength of the short spring arm is set to give a foil off wheel torque greater than that needed to peel the foil, but substantially less than that needed to break the foil; this spring 234 force controls the loads applied to the foil during peeling making the indexing action more consistent, smoother and gentler.

Figure 7:
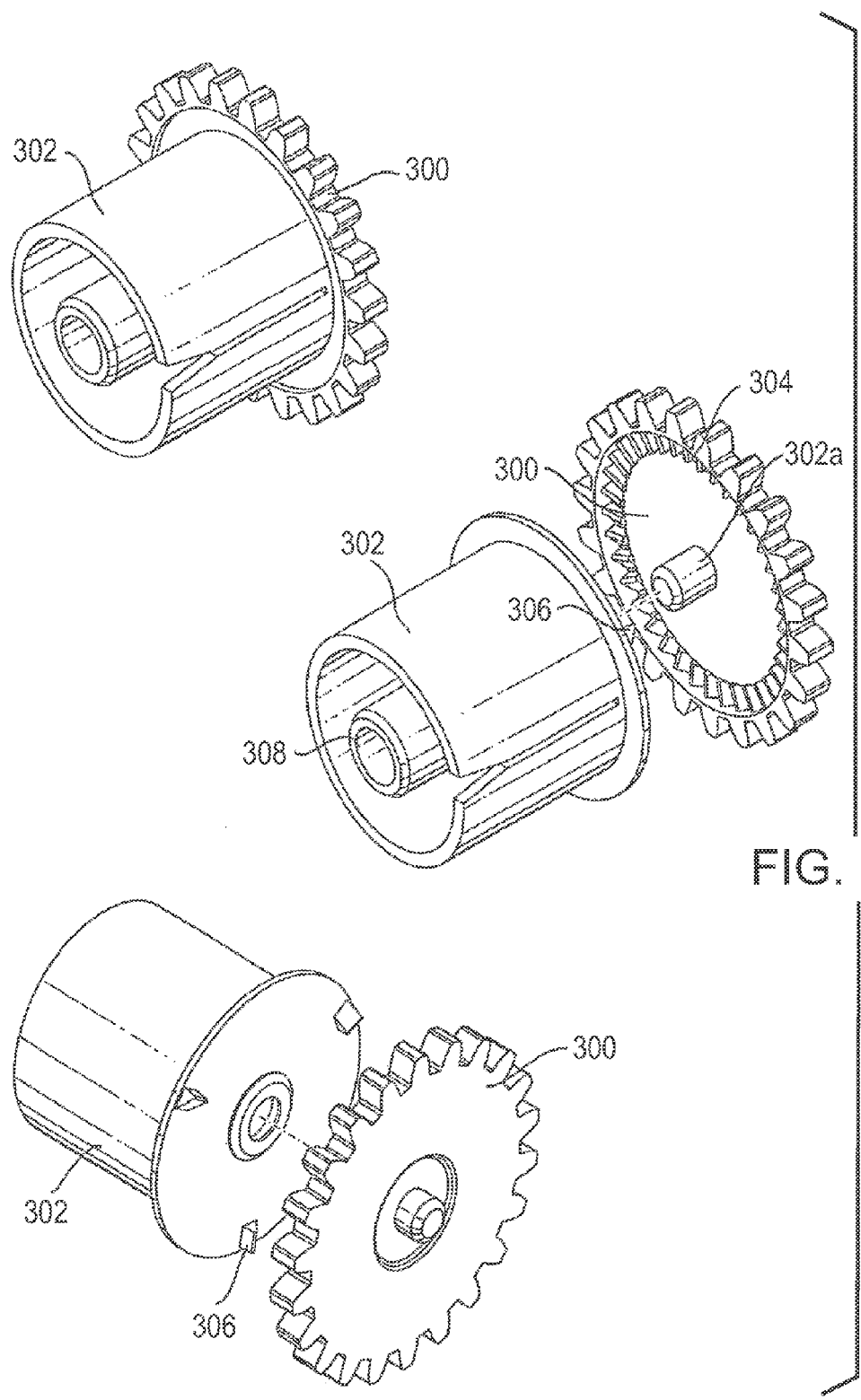
FIG. 7 shows a wobbler mechanism in accordance with another aspect of the invention.

FIG. 7 illustrates an alternative embodiment of the invention which utilises a "wobble" assembly instead of the Vernier spring assembly. Both systems both work using the same slippage concept. In this case, the index wheel (not shown) drives a gear wheel 300 through a gearing interaction. The gear wheel receives a foil haul off wheel 302 on a spindle 302a. The gear wheel 300 has a series of indentations 304 close to its outer rim. On the foil haul off wheel 302 there are 3 dog teeth 306 spaced equidistant around the base of the wheel so that at any one time, one dog tooth 306 can engage one of the indentations 304 on the gear wheel 300. The spindle 302a of the gear wheel 300 is mounted on a spring (not shown) in the foil haul off wheel shaft 308 so that the wheel 300 can wobble to a slight degree. At forces greater than the torque required to unpeel the medicament carrier but substantially less that that required to break the medicament carrier, the gear wheel 300 wobbles/disturbs the interaction between the indentation 304 and the dog tooth 306 on the foil haul off wheel 302 and slippage occurs; the gear wheel 300 now rotates independently of the foil haul off wheel 302. Thus, the gear ratio between the index wheel and the foil haul off wheel is maintained at one-to-one, irrespective of the increase in diameter of the foil haul off wheel as the foil is wound around it.

FIG. 8 shows a medicament dispenser in accord with the present invention, comprising a body 400, a holder 402, refill cassette 404 and electronic display 406. The holder 402 is shaped to fit snugly inside body 400 and is fixed to a point on the body (not shown) about which it rotates. Stops 408, 410 protrude from the holder 402 and prevent the holder 402 from rotating more than about 180° relative to the body 400. The stops 408, 410 also provide two defined positions of the holder 402 within the body 400. One position is defined by stop 408 meeting with body edge 412 and the other position defined by stop 410 meeting with body edge 414 when the holder has been rotated relative to the body. The area between stops 408 and 410 is shaped to form a thumb or finger grip 416 for the user of the device. The holder 402 forms a shell into which the refill cassette 404 snugly fits.

The refill cassette 404 comprises a shell containing the medicament carrier (not shown) and a mechanism for opening the carrier (not shown) for the medicament to be accessed. The refill cassette 404 has a raised portion 418 at one end on both sides along its width so that this part of the refill cassette 404 is at least the same depth as the part of the holder 420 which receives the refill cassette 404. This allows the position of the cassette 404 within the holder 402 to be fixed such that the ridge 418 protrudes from the holder 402 but the rest of the cassette 404 is contained within the holder 402.

The refill cassette 404 also has a mouthpiece (not shown) and an indexing lever 422 for indexing the medicament carrier within the cassette 404.

Figure 9B:
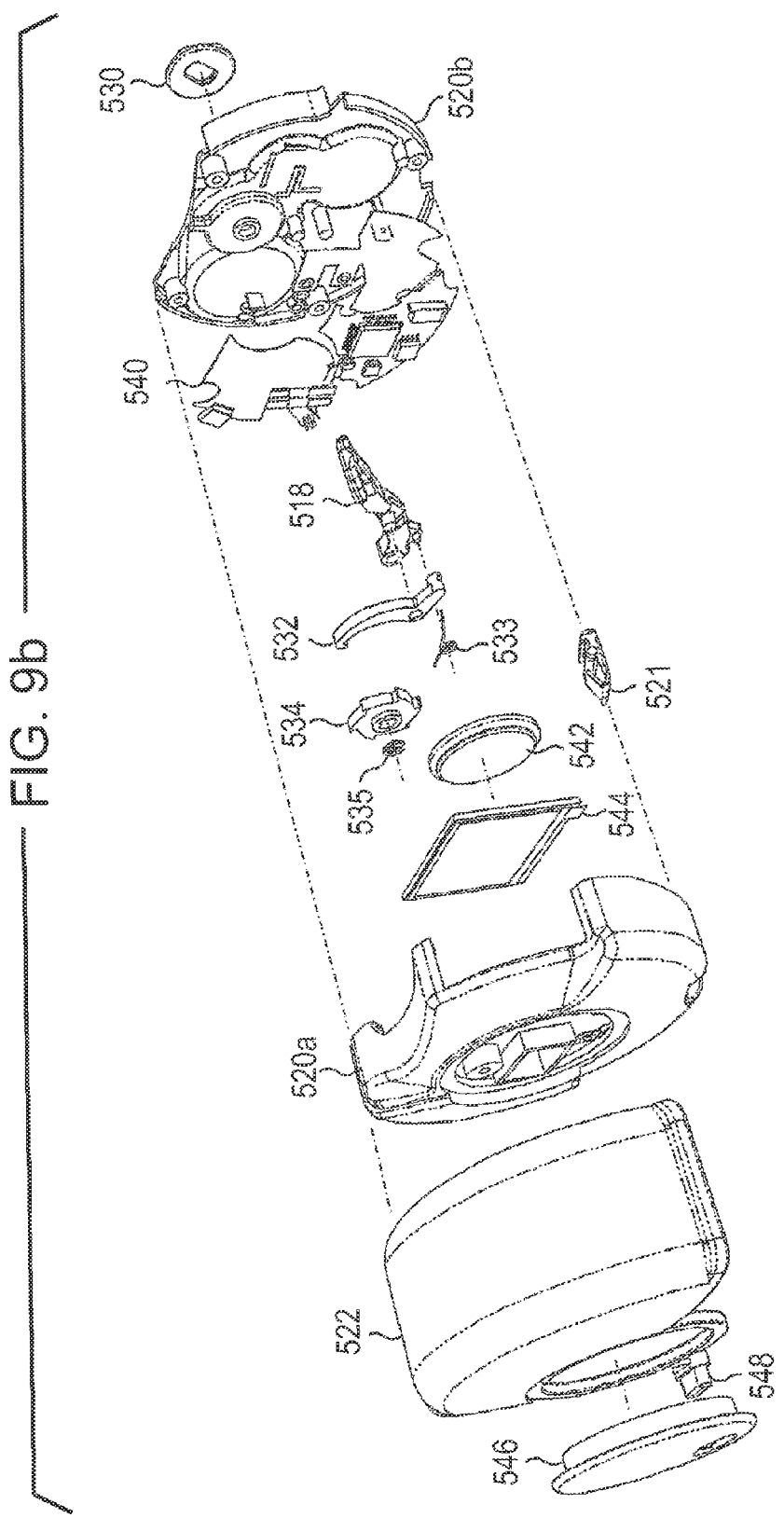

FIGS. 9a and 9b respectively show a refill cassette and cassette holder/body herein. The cassette of FIG. 9a has a cassette body comprising cover 504a and backplate 504b which receives a medicament carrier 500 in the form of an elongate blister strip behind manifold 501. The cassette body and manifold 501 in turn connect to mouthpiece 503 for the inhalation of released medicament by a patient. The medicament carrier strip 500 and lid foil 502 are positioned on disposable wheels. The index wheel 506 is a five pocket wheel mounted on haul shaft 505, and the foil wheel 508 is a fixed diameter cylinder coupled by gear 507. The lid foil 502 is positioned on the cylinder 508 by passing the foil tail into a slot and winding the wheel to tighten the foil onto it. Ratchet spring 504 is provided to the index wheel 506 so that its position is fixed after assembly and cannot be altered until the cassette is securely installed in a base unit, and so the cassette can be removed and reassembled during use without losing the lid foil and medicament carrier strip positions.

Haul wheel 512 engages directly with the index wheel 506. The haul wheel 512 is drivable through Vernier spring assembly comprising Vernier spring 516; Vernier gear 514; and Vernier spacer 515 to index driver wheel 510 mounted on index shaft 511. It will be appreciated that the index driver wheel 510 is drivable by a driver mechanism (mounted in the cassette holder 520a, 520b as shown in FIG. 5b) to advance the medicament carrier 500 in controlled fashion.

The cassette holder comprises a cover 520a and backplate 520b secured together by catch 521. The backplate 520b is shaped to mate with the backplate 504b of the cassette. When the cassette is so received, rotatable assembly cover 522 covers a part of the holder-cassette assembly about which it is rotatable. Driver 530 mounted on the holder backplate 520b is coupled to index shaft 511 and hence to the Vernier mechanism 514, 515, 516 of the cassette for indexing/advancing the medicament carrier 500.

The driver 530 is drivable by the action of lever arm 518, which is moderated by ratchet mechanism comprising ratchet arm 532; ratchet spring 533; ratchet wheel 534 and e-clip 535. In more detail, the driver 530 drives the index driver wheel 510 one fifth of a turn for each full travel of the lever 518. The resulting rotary motion of the index driver wheel 510 is delivered to the foil haul off assembly 512, 514, 515, 516. Each one fifth of a turn of the index wheel 510 delivers one fifth of a turn to the haul wheel 512 which drives the Vernier spring 516. The Vernier spring 516 is designed to allow the foil haul off wheel 514 to run more slowly than the index wheel 506 (necessary as the foil winds onto the wheel and the diameter of the effecting winding surface increases), and to resolve the difference in the amount of rotation of the two wheels sufficiently accurately for the foil advance action to be smooth, consistent and reliable. The overall action of the Vernier mechanism is similar to that described in FIGS. 3 to 6c.

The holder of FIG. 9b is also provided with electronic capability in the form of a printed circuit board 540; button cell 542; LCD display 544; screen 546; and on/off button 548. The electronic components may, in aspects, be configured to enable display of information to a user e.g. relating to actuation and release of medicament from the dispenser.

It may be appreciated that any of the parts of the dispenser or cassette which contact the medicament suspension may be coated with materials such as fluoropolymer materials (e.g. PTFE or FEP) which reduce the tendency of medicament to adhere thereto. Any movable parts may also have coatings applied thereto which enhance their desired movement characteristics. Frictional coatings may therefore be applied to enhance frictional contact and lubricants (e.g. silicone oil) used to reduce frictional contact as necessary.

The medicament dispenser of the invention is suitable for dispensing medicament, particularly for the treatment of respiratory disorders such as asthma and chronic obstructive pulmonary disease (COPD), bronchitis and chest infections. Appropriate medicaments may thus be selected from, for example, analgesics, e.g. codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and, pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (eg as the fumarate salt) in combination with an anti-inflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A medicament dispenser for use with a medicament carrier having a plurality of pockets for containing medicament wherein said pockets are spaced along the length of and defined between two peelable sheets secured to each other, said dispenser having an internal dispensing mechanism for accessing said medicament contained within said medicament carrier, said mechanism comprising,
   a) an opening station for receiving a pocket of said medicament carrier;
   b) a peeling arrangement positioned to engage a base sheet and a lid sheet of a pocket which has been received in said opening station for peeling apart said base sheet and said lid sheet, to open said pocket, said peeling arrangement including a lid driving arrangement for pulling apart a lid sheet and a base sheet of a pocket that has been received at said opening station, said lid driving arrangement comprising a wheel on which said lid sheet is wound, said wheel having an effective winding surface, the diameter of which increases as more lid sheet is wound about said wheel;
   c) an outlet, positioned to be in communication with an opened pocket through which a user can remove medicament from said opened pocket;
   d) an indexing arrangement for indexing in communication with said outlet, pockets of a medicament carrier in use with said medicament dispenser, said indexing arrangement being interconnected with said lid driving arrangement such that movement of one correlates with the movement of the other; and
   e) in communication with the indexing arrangement and lid driving arrangement, a clutch arrangement for compensating for an increase in diameter of said effective winding surface of the lid driving arrangement by allowing for slippage when tension in the lid sheet is greater than the force required to pull apart the lid sheet and the base sheet, said clutch arrangement comprising a gearing surface defining plural gear engagement positions; and plural gear teeth for engaging said plural gear engagement positions to enable transmission of a drive therebetween, wherein the gearing surface and the plural gear teeth are configured and arranged such that at any one time only a single one of the gear teeth is in driving engagement with a gear engagement position.

2. A medicament dispenser according to claim 1, wherein the gearing surface and the plural gear teeth are arranged such that the number of individual gear positions definable is equal to the number of gear engagement positions multiplied by the number of gear teeth.

3. A medicament dispenser according to claim 1, wherein the gearing surface defines from 20 to 100 gear engagement positions.

4. A medicament dispenser according to claim 1, wherein the number of gear teeth is from 2 to 20.

5. A medicament dispenser according to claim 1, wherein the gear engagement positions are equally spaced and the gear teeth are offset relative thereto.

6. A medicament dispenser according to claim 1, wherein the gear engagement positions are equally spaced and the gear teeth are located on a wobbling element capable of wobbling the gear teeth to plural offset positions.

7. A medicament dispenser according to claim 1, wherein the clutch arrangement is non-integral with either of the lid driving arrangement or the indexing arrangement.

8. A medicament dispenser according to claim 1, wherein the gearing surface comprises a gear wheel.

9. A medicament dispenser according to claim 1, wherein the gear teeth are arranged in ratchet form.

10. A medicament dispenser according to claim 1, wherein the gearing surface and the plural gear teeth are biased for engagement with one another.

11. A medicament dispenser according to claim 1, wherein said indexing arrangement comprise a rotatable index wheel having recesses therein, said index wheel being engageable with a medicament carrier in use with said medicament dispenser such that said recesses each receive a respective pocket of the base sheet of a medicament carrier in use with said medicament dispenser.

12. A medicament dispenser according to claim 1, wherein said indexing arrangement comprises an indexing ratchet which is moveable between a locked position whereby said ratchet engages a pocket on said medicament carrier and prevents further peeling thereof, and a release position allowing free movement of said medicament carrier, and actuation of said medicament dispenser actuates said lid driving arrangement and releases said index ratchet from said medicament carrier to allow peeling thereof.

13. A medicament dispenser according to claim 1 further comprising an indexing lever for actuating said dispenser wherein said indexing lever is interconnected with said indexing arrangement.

14. A medicament dispenser according to claim 1 wherein the medicament is in powdered or compacted solid form.

15. A medicament dispenser according to claim 14, wherein the medicament is in powdered form and comprises a drug which is selected from the group consisting of albuterol, salmeterol, fluticasone propionate and beclomethasone dipropionate and salts or solvates thereof and any combination thereof.

16. A medicament dispenser according to claim 15, wherein said combination comprises salmeterol xinafoate and fluticasone propionate.

17. A medicament dispenser according to claim 14, wherein the medicament additionally comprises an excipient.

18. A medicament dispenser according to claim 17, wherein the excipient is a sugar.

19. A medicament dispenser according to claim 1 which is a dry powder inhaler.

20. A medicament dispenser according to claim 19, wherein the wheel of the lid driving arrangement on which the lid sheet is to be wound is a driven wheel mounted for rotation about an axis, wherein the lid driving arrangement further has a drive wheel for driving rotation of the driven wheel which is co-axially mounted with the driven wheel, and wherein the gear teeth and gearing surface are provided on different ones of the driven and drive wheels to enable drive to be transmitted from the drive wheel to the driven wheel.

21. A medicament dispenser according to claim 20, wherein one of the wheels includes a clutch plate on which is formed the respective one of the gear teeth and gearing surface.

22. A medicament dispenser according to claim 21, wherein the clutch plate has the form of a Vernier spring.

23. A medicament dispenser according to claim 20, wherein the gear teeth and gearing surface are a first set of gear teeth and first gearing surface, the internal dispensing mechanism has a second set of teeth and a second gearing surface, one of which is provided by the driven wheel, and wherein the second gearing surface and at least one of the second set of teeth are adapted in use to engage each other to intermittently restrain rotation of the driven wheel by the drive wheel thereby to cause slippage between the first gear teeth and first gearing surface to compensate for an increase of the effective winding surface of the driven wheel.

24. A medicament dispenser according to claim 23, wherein the driven wheel includes a co-axially arranged clutch plate having a first face facing the drive wheel and provided with the respective one of the first gear teeth and first gearing surface and a second opposite face provided with the respective one of the second set of gear teeth and second gearing surface.

25. A medicament dispenser according to claim 24, wherein the clutch plate has the form of a Vernier spring.

26. A medicament dispenser according to claim 20, wherein the lid driving arrangement comprises a slip mechanism for enabling intermittent slippage between the gear teeth and gearing surface to compensate for an increase of the effective winding surface of the driven wheel.

27. A medicament dispenser according to claim 20, wherein said indexing arrangement comprise a rotatable index wheel having recesses therein, said index wheel being engageable with a medicament carrier in use with said medicament dispenser such that said recesses each receive a respective pocket of the base sheet of the medicament carrier.

28. A medicament dispenser according to claim 27, wherein the index wheel is coupled to the drive wheel such that rotation of the index wheel causes rotation of the drive wheel.

29. A medicament dispenser according to claim 28, wherein the index and drive wheels are rotatably coupled by a gear arrangement.

30. A medicament dispenser according to claim 29, wherein the index and drive wheels are gear wheels in meshing engagement with one another.

31. A medicament dispenser according to claim 28, wherein the index and drive wheels are rotatably coupled by a crank arrangement.

32. A medicament dispenser according to claim 28 further comprising an actuating member for actuating the internal dispensing mechanism, said actuating member being coupled to the index wheel.

33. A medicament dispenser according to claim 32, wherein the actuating member is manually-operable by a user of the dispenser.

34. A medicament dispenser according to claim 20, wherein the gearing surface and plural gear teeth are angularly arranged about the common axis in facing relation to each other.

35. A medicament dispenser according to claim 1, wherein the gearing surface and plural gear teeth are angularly arranged about a common rotation axis in facing relation to each other.

36. A medicament dispenser according to claim 35, wherein the gearing surface and plural gear teeth are respectively arranged in planes essentially orthogonal to the common rotation axis.

37. A method of dispensing a medicament comprising:
(a) providing a medicament dispenser having a medicament carrier having a plurality of pockets containing medicament wherein said pockets are spaced along the length of and defined between two peelable sheets secured to each other, said dispenser having an internal dispensing mechanism for accessing said medicament contained within said medicament carrier, said mechanism comprising,
  i) an opening station for receiving a pocket of said medicament carrier;
  ii) a peeling arrangement positioned to engage a base sheet and a lid sheet of a pocket which has been received in said opening station for peeling apart said base sheet and said lid sheet, to open said pocket, said peeling arrangement including a lid driving arrangement for pulling apart a lid sheet and a base sheet of a pocket that has been received at said opening station, said lid driving arrangement comprising a wheel on which said lid sheet is wound, said wheel having an effective winding surface, the diameter of which increases as more lid sheet is wound about said wheel;
  iii) an outlet, positioned to be in communication with an opened pocket through which a user can remove medicament from said opened pocket;
  iv) an indexing arrangement for indexing in communication with said outlet, pockets of the medicament carrier, said indexing arrangement being interconnected with said lid driving arrangement such that movement of one correlates with the movement of the other; and
  v) in communication with the indexing arrangement and lid driving arrangement, a clutch arrangement for compensating for an increase in diameter of said effective winding surface of the lid driving arrangement by allowing for slippage when tension in the lid sheet is greater than the force required to pull apart the lid sheet and the base sheet, said clutch arrangement comprising a gearing surface defining plural gear engagement positions; and plural gear teeth for engaging said plural gear engagement positions to enable transmission of a drive therebetween,
  wherein the gearing surface and the plural gear teeth are configured and arranged such that at any one time only a single one of the gear teeth is in driving engagement with a gear engagement position; and
(b) dispensing medicament from the medicament dispenser.

* * * * *